United States Patent [19]

Krueger

[11] Patent Number: 5,795,307
[45] Date of Patent: Aug. 18, 1998

[54] SHUNT TAP APPARATUS AND METHOD

[76] Inventor: John A. Krueger, 17900 Anthony La., Brookfield, Wis. 53045

[21] Appl. No.: 841,264

[22] Filed: Apr. 29, 1997

[51] Int. Cl.$^6$ ............................................. A61B 5/00
[52] U.S. Cl. ............................................. 600/561; 604/9
[58] Field of Search ........................... 600/561, 576, 600/584, 488; 604/7, 8, 9, 10

[56] References Cited

U.S. PATENT DOCUMENTS

| | | | |
|---|---|---|---|
| 3,958,558 | 5/1976 | Dunphy et al. | 600/561 |
| 4,127,110 | 11/1978 | Bullara | 600/561 |
| 4,231,376 | 11/1980 | Lyon et al. | 600/561 |
| 4,385,636 | 5/1983 | Cosman | 600/561 |
| 4,660,568 | 4/1987 | Cosman | 600/561 |
| 4,676,255 | 6/1987 | Cosman | 600/561 |

*Primary Examiner*—Max Hindenburg
*Assistant Examiner*—Charles Marmor, II
*Attorney, Agent, or Firm*—Skarsten Law Offices S.C.

[57] ABSTRACT

A shunt tap device is provided for use in sensing CSF pressure data in a shunt implanted in a subject, wherein the shunt comprises a valve having a reservoir, and first and second catheters providing CSF flow paths toward and away from the valve, respectively. The shunt tap device is provided with a hollow needle for temporarily forming an aperture through the wall of the reservoir, to communicate with CSF contained therein. A length of flexible microbore tubing extends from the needle to a coupling, such as a Touhy-Borst connector, which is disposed to receive the pressure transducer component of a pressure monitoring device into a narrow fluid enclosure, collectively formed by the hollow needle, tubing, and a portion of the connector. The fluid enclosure is filled with a saline fluid or the like, having properties similar to CSF. The connector is tightened to seal the saline fluid within the fluid enclosure, and also to retain the pressure transducer in the enclosure, in contact with the saline fluid. By means of such arrangement, CSF pressure data is transmitted from the reservoir to the pressure transducer through the saline fluid, enabling a pressure reading to be provided by the monitor. At the same time, the arrangement allows only negligible amounts of CSF to flow out of the reservoir.

19 Claims, 6 Drawing Sheets

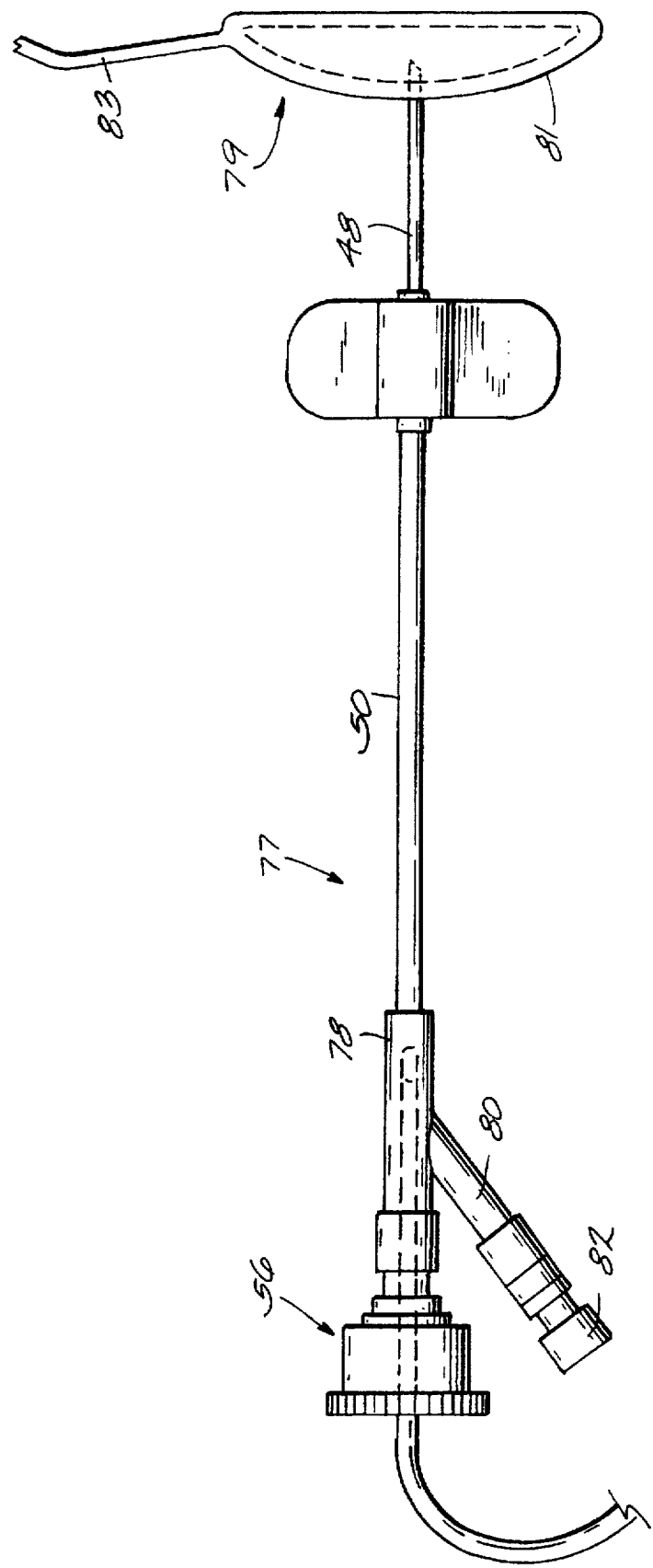

SHUNT TAP APPARATUS AND METHOD

BACKGROUND OF THE INVENTION

The invention disclosed and claimed herein is generally directed to apparatus and method for monitoring or sensing pressure data pertaining to cerebrospinal fluid (CSF) in a shunt system implanted in a patient or other subject. More particularly, the invention pertains to apparatus and method of such type which can provide shunt pressure data in real time, and with substantially improved accuracy. Even more particularly, the invention pertains to apparatus and method of such type for providing information pertaining to a shunt pressure wave form, and for recording such information in printed or other form for subsequent referral and use.

As is well known, a shunt or shunt system is an arrangement for controllably draining excessive CSF away from the ventricles or cavities of a subject's brain or spine. A common brain shunt system generally comprises a valve having a specified pressure rating, and two flexible tubes or catheters, referred to as the ventricular and peritoneal catheters, respectively. The ventricular catheter is positioned to carry CSF from a ventricle to the valve. If the intracranial pressure (ICP) in the valve exceeds the valve opening pressure rating, the valve opens to allow CSF to flow away therefrom through the peritoneal catheter, typically to the region of the subject's abdomen. A shunt system further includes a reservoir in proximal relationship to the valve, i.e., on the "upstream" side thereof. Shunt systems are extensively used to treat conditions such as hydrocephalus. Respective components of a shunt system are placed or implanted under the skin of a user.

It will be readily apparent that the pressure rating of a shunt system valve must be properly selected with respect to the ICP of a patient or other shunt user. If the rating is too low or too high, the valve will be opened or closed, respectively, in the opposite mode of valve operation than desired. Even if a proper match is initially established between ICP and shunt valve pressure rating, a patient's ICP can change over time. Moreover, occlusions or obstructions may gradually develop in one or both catheters of a shunt, restricting fluid flow therethrough.

It frequently would be very desirable, when either catheter occlusion or improper valve opening pressure rating is suspected, to be able to quickly and accurately measure CSF pressure level in a shunt system. However, such measurement currently is made by means of a manometer. As is well known, a manometer comprises a graduated tube, which is held in a vertical orientation and contains a column of water or other fluid. The manometer tube is open at its top, so that atmospheric pressure acts against the water column. To measure shunt fluid pressure, CSF flowing through the reservoir of the shunt valve, which would otherwise pass through the peritoneal catheter, is redirected to the bottom of the manometer tube. As CSF enters the tube, the column is raised upward, until the weight of the increased column, in combination with atmospheric pressure, exactly equals the pressure in the shunt. The top of the column, or a ball or like object floating thereon, provides an indication of such pressure.

A manometer is an open system in that it requires fluid from another system to enter the tube referenced to atmospheric pressure. Because CSF must, accordingly, be drawn out of the shunt system, the pressure thereof drops below its true level. That is, the pressure shown by the manometer will not accurately represent the actual CSF pressure in the shunt, at the time the measurement procedure began. Moreover, it may require several minutes for CSF to flow into the manometer from the shunt, and to bring the manometer into a state of equilibrium for a pressure reading. During such period, the patient must generally stay very still, in a supine or other specified position. These conditions may be very difficult to achieve, if the patient is, for example, a crying infant. In addition, some patients experience headaches resulting from high intracranial pressure, whereas other patients experience headaches from low ICP. A manometer will generally not read pressures that are lower than its "zero" reference point. Accordingly, such devices generally cannot be used by a physician to assist in determining which type of pressure condition is causing a patient's headache.

It has been recognized by those of skill in the art that periodic variation of ICP in a patient, represented by specific pressure wave patterns or wave forms, can be very useful in diagnosing conditions such as hydrocephalus. This is noted, for example, in a publication entitled "Diagnosis of Hydrocephalus by CSF Pulse-Wave Analysis: A Clinical Study", Fault et. al., *Surgical Neurology*, Vol. 15, No. 4, p. 283, published April, 1981 by Little, Brown & Co. where ICP and recorded pressure wave forms were measured by tapping directly into the ventricle. Such pressure waveforms can also be very useful in recognizing certain shunt malfunctions, such as incorrect valve pressure rating and catheter blockage if the ICP and pressure wave forms are measured from an implanted shunt. However, a manometer is not able to provide any ICP waveform data or diagnosis of cerebral conditions and cannot generate a printed or other record thereof.

SUMMARY OF THE INVENTION

The present invention comprises shunt tap apparatus for use in sensing CSF pressure data in a shunt implanted in a subject, wherein the shunt includes a reservoir lying along a CSF path of flow. The shunt tap apparatus comprises means for temporarily forming an aperture through the wall of the reservoir, to communicate with CSF contained therein. The apparatus further comprises coupling means for selectively engaging a pressure transducer comprising a component of a pressure monitoring device of specified type. Means are positioned between the aperture forming means and the coupling means for transmitting CSF pressure data from the reservoir to the pressure transducer, while at the same time restricting CSF in the reservoir from passing through the aperture.

In a preferred embodiment of the invention, the aperture forming means comprises a hollow needle, having a specified maximum gauge. The pressure transmissive means comprises a fluid enclosure extending between the needle and the pressure transducer, together with a selected fluid, preferably a saline solution, which substantially fills the fluid enclosure. In a useful embodiment, the coupling means comprises the catheter sealing component of a conventional Touhy-Borst connector, which is disposed to receive the pressure transducer of a fiber optic ICP monitoring device. In another embodiment, the coupling means comprises a luer lock disposed for use with a pressure transducer of a strain gauge ICP monitoring device.

The invention is also directed to a shunt tap method for use in sensing CSF pressure data in a shunt implanted in a subject. The method includes the steps of temporarily forming an aperture through the shunt reservoir, in communication with CSF contained therein; transmitting CSF pressure data through the aperture from the reservoir to a pressure transducer at a selectively spaced apart location, while at the same time restricting CSF in the reservoir from passing through the aperture; and operating the pressure transducer to generate an information signal of selected type representing the transmitted CSF pressure data.

In a preferred embodiment, the method includes the further step of recording or storing the selected information signal, for example by printed or electronic means, for subsequent use and reference. In another embodiment, the method includes the additional step of blocking an outlet of a shunt valve, of which the reservoir is a component. The pressure in the reservoir will thereupon become substantially the same as the intracranial pressure in the ventricle of the subject using the shunt. Accordingly, the selected information signal will represent the ICP of the subject.

OBJECTS OF THE INVENTION

An object of the invention is to provide apparatus and method for acquiring data pertaining to CSF pressure in a shunt system with substantially improved accuracy.

Another object is to provide an apparatus and method of the above type which does not require that any significant amount of CSF be removed from the shunt system, and which therefore maintains the shunt as a closed pressure system while pressure related data is being acquired.

Another object is to provide apparatus and method of the above type for providing shunt pressure data in substantially real time.

Another object is to provide apparatus and method of the above type which can be adjusted to provide a negative ICP reading, in order to readily indicate a low ICP condition.

Another object is to provide an apparatus and method of the above type which can be readily employed to monitor ICP mean pressure, as well as ICP wave forms, in a patient with which the shunt is used.

Another object is to provide apparatus and method of the above type wherein pressure data is acquired from a reservoir or other component lying along the CSF path of flow in proximal relationship with the shunt system valve, i.e., "upstream" from the valve, so that monitored pressure will be an accurate assessment of the implanted shunt, and the pressure waveform will not be dampened out by the valve element.

Another object is to provide an apparatus and method of the above type which can be readily used to record or store ICP wave forms and other pressure related data acquired from the shunt system.

Another object is to provide an apparatus and method for acquiring pressure related data from a shunt system, wherein it is not necessary to keep the patient in a specified position for a period of time.

Another object is to provide apparatus and method of the above type for dynamic monitoring of ICP, i.e., acquiring pressure related data from a patient as the patient assumes different positions These and other objects of the invention will become more apparent from the ensuing specification, taken together with the accompanying drawings.

BRIEF DESCRIPTION OF THE DRAWINGS

FIG. 8 shows a modification of the embodiment shown in FIG. 3.

FIG. 9 shows a further modification of the embodiment shown in FIG. 3.

DETAILED DESCRIPTION OF THE PREFERRED EMBODIMENT

Figure 1:
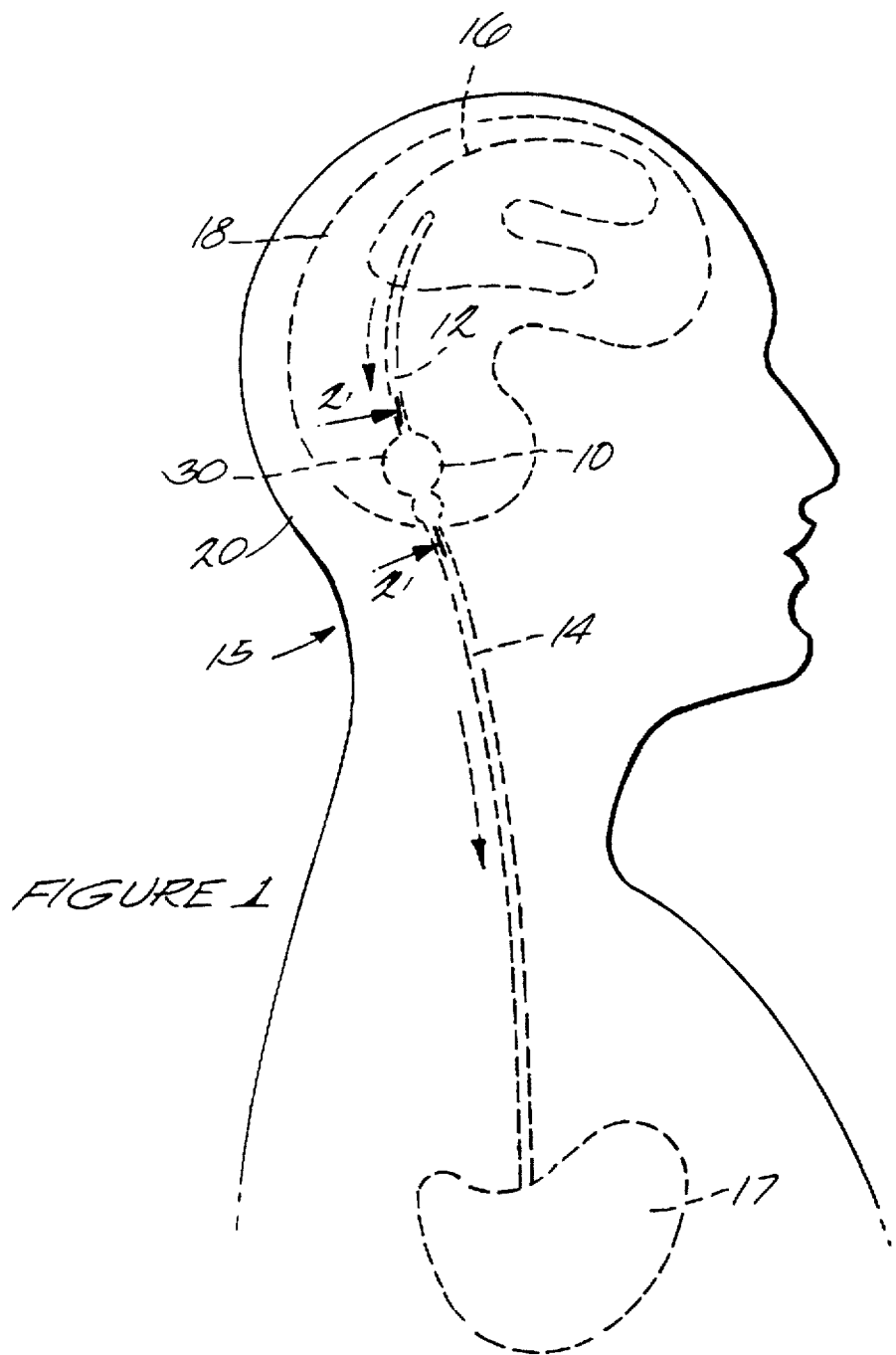
FIG. 1 is a schematic view showing the basic components of a shunt system positioned with respect to a subject.

Referring to FIG. 1, there is shown a shunt system 15 of conventional type, generally comprising a valve 10, ventricular catheter 12 and peritoneal catheter 14. Ventricular catheter 12 extends from a ventricle 16, within the brain 18 of a subject 20, to the valve 10 in order to carry CSF to the valve as described above. Valve 10, described hereinafter in further detail, has a reservoir 30 and an opening pressure rating corresponding to a physician specified ICP in ventricle 16. When ICP increases above valve opening pressure, excessive CSF will drain out of the ventricle 16 and into the valve 10. Thereupon, valve 10 opens, allowing the CSF to flow into peritoneal catheter 14, and therethrough to the subject's peritoneal or stomach region 17. In accordance with standard practice, the valve is implanted subcutaneously and positioned with the bottom of the valve against the skull, approximately at ear level. Also, peritoneal catheter 14 is kept beneath the epidermal layer of the subject. The flow direction of CSF through shunt 15 is indicated by arrows in FIG. 1.

As is well known to those of skill in the art, shunt systems are also available which drain into the heart or other regions, rather than the peritoneal region. Also, there are shunts which drain excess fluid from other cavities besides those of the brain, such as the lumbar-subarachnoid space in the spine. Moreover, a shunt implant may comprise no more than a ventricular or other primary catheter and a reservoir, such as may be used for chemotherapy. It is anticipated that an embodiment of the invention may be used with a wide range of such shunt system variations and configurations.

Figure 2:
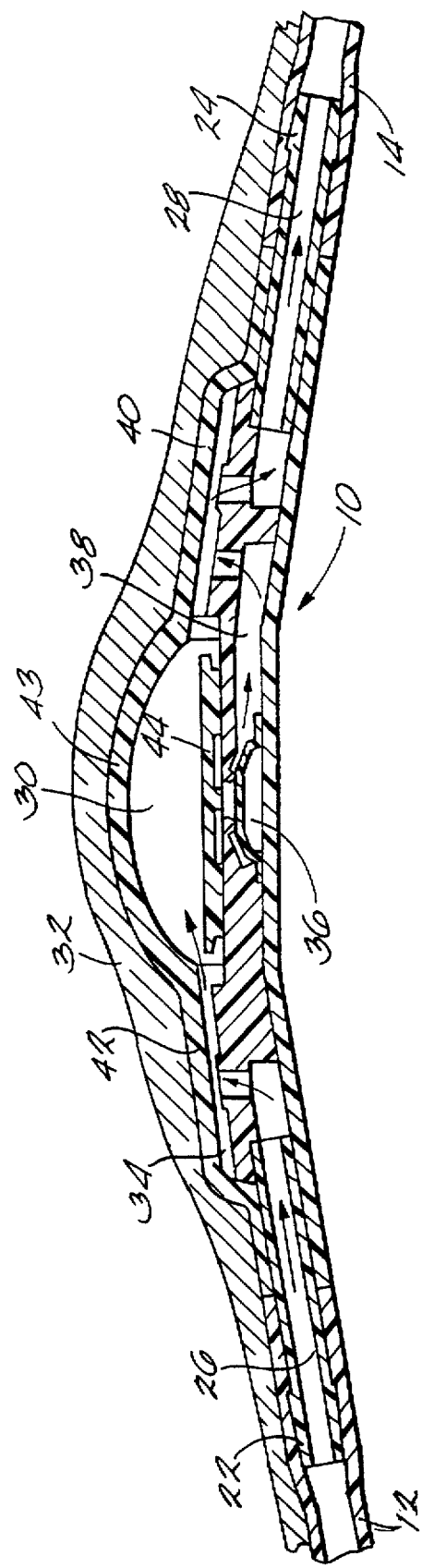
FIG. 2 is a sectional view taken along lines 2—2 of FIG. 1, to show the general construction of a shunt system valve.

Referring to FIG. 2, there is shown valve 10 comprising, for example, a valve product manufactured by NeuroCare, Inc., assignee herein, and identified by the trademark LPV, a registered trademark of NeuroCare. Such valve product is further described in U.S. Pat. Nos. 4,364,395; 4,464,168; and 3,769,982.

Referring further to FIG. 2, there is shown valve 10 provided with proximal connector 22 and distal connector 24 for respectively coupling the inlet port 26 of valve 10 to ventricular catheter 12, and the outlet port 28 thereof to peritoneal catheter 14. More particularly, connectors 22 and 24 are inserted into the ends of catheters 12 and 14, respectively. Valve 10 is further provided with a dome or reservoir 30, comprising an enlarged fluid-containing chamber which is covered by the scalp 32 of subject 20. CSF flows into reservoir 30 from inlet port 26 through a reservoir inlet passage 34. When pressure in the reservoir 30 exceeds the opening pressure rating of valve 10, a valve element 36 is urged downwardly, as viewed in FIG. 2. Such pressure rating is selected from a range on the order of 5–50 mm of water for low pressure valve or 51–110 mm of water for a medium pressure valve. Thereupon, CSF flows from reservoir 30 into reservoir outlet passage 38, and therethrough to outlet port 28.

FIG. 2 further shows valve 10 provided with distal and proximal occluders 40 and 42, respectively. When distal occluder 40 is urged downwardly, as viewed in FIG. 2, by pressing through scalp 32, reservoir outlet passage 38 is closed to prevent CSF from flowing therethrough into peritoneal catheter 14. Similarly, when proximal occluder 42 is urged downwardly, as viewed in FIG. 2, reservoir inlet port 34 is closed, to prevent CSF from flowing into reservoir 30.

The wall 43 of reservoir 30, in contact with scalp 32 of subject 20, is formed of material such as self-sealing silicone, as described hereinafter in further detail. A needle guard 44, positioned between reservoir 30 and valve element 36, is likewise described hereinafter.

Figure 3:
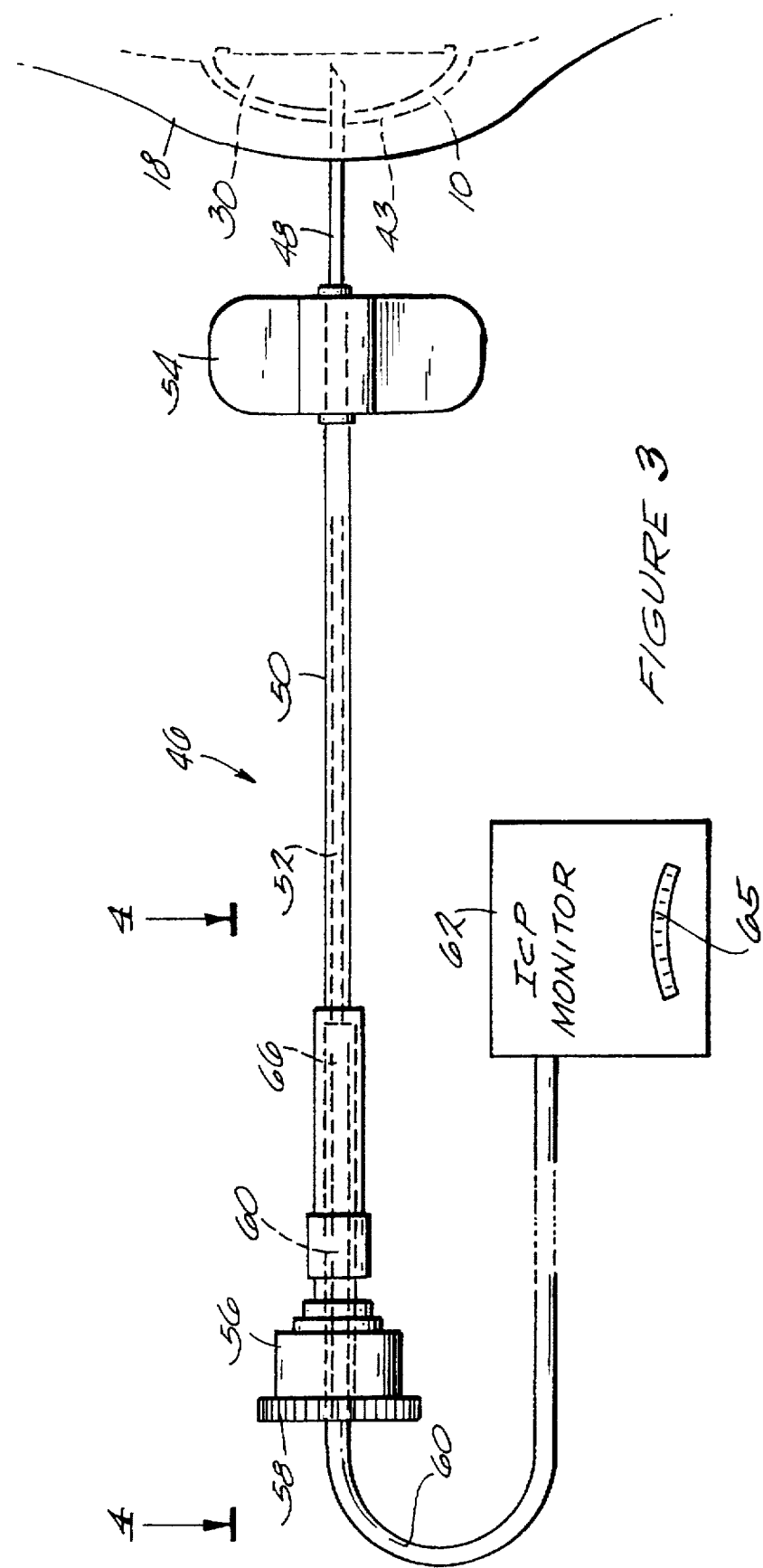
FIG. 3 is a schematic view showing an embodiment of the invention.

Referring to FIG. 3, there is shown a shunt tap 46 comprising an embodiment of the invention. Tap 46 includes a beveled tip hollow needle 48, no greater than on the order of 25 gauge, and usefully ¾ of an inch in length. The needle 48 is joined to a length of flexible microbore tubing 50, usefully 2.5 inches in length, provided with a passage 52 therethrough of microbore diameter i.e., having an inner diameter on the order of 0.02 inch. Hollow needle 48 is joined to tubing 50 so that the passage through the needle (not shown) is in communication with passage 52. In operation, needle 48 is inserted through the scalp of subject 20, and through the wall of valve 10 into reservoir or dome 30. To provide strain relief for the needle, a flat plastic butterfly configuration 54 is usefully employed to join needle 48 and tubing 50 together, and the tabs of butterfly 54 are taped to the head of subject 20. While not specifically shown, tube 50 is preferably provided with a horizontal rather than a vertical orientation. This will avoid distortions in pressure measurement resulting from the effects of gravity acting on fluid in a vertical column.

If reservoir 30 is formed of self-sealing silicone, the aperture through the wall 43 of reservoir 30 will sealably close, after needle 48 is removed therefrom. If needle 48 is no greater than twenty-five gauge, reservoir 30 can be "stuck" hundreds of times, without causing leakage therein. The needle guard 44 of valve 10 protects valve element 36 from thrusts of needle 48.

Referring further to FIG. 3, there is shown a catheter coupling device 56 joined to the end of tubing 50 opposite needle 48. In a preferred embodiment, catheter coupling device 56 comprises a device known as a Touhy-Borst connector. Such connector is provided with a nut 58, which is rotatable to form a sealed connection with a catheter 60, of an ICP monitor device 62. ICP monitor 62 comprises one of a number of devices currently available for directly sensing ICP in a brain ventricle. However, in the past, use of such devices have required that a hole be formed through a patient's skull, so that a pressure sensor could be inserted therethrough into the patient's ventricle. As further described hereinafter, the shunt tap of the invention enables an ICP monitor device to be used to determine ICP, as well as pressure data pertaining to a shunt, without the need for such invasive procedure. ICP monitors of the above type generally have a pressure sensor or transducer 66 housed in the tip of the catheter 60, which is brought into contact with fluid to measure pressure thereof. In accordance with the invention, the passage 52 through tube 50 of shunt tap device 46 is filled with a saline fluid 64 (shown in FIG. 4), a solution of conventional type, which is very similar to CSF. Such fluid is inserted into passage 52 of tube 50, such as by means of a syringe, before needle 48 is inserted to form an aperture through the wall 43 of reservoir 30. The fluid 64 extends partly into the catheter coupling device 56. After placing the fluid 64 in the tube 50 the Touhy-Borst connector is tightened, to close or pinch off catheter 60 at a point spaced apart from pressure transducer 66. Such operation of the Touhy-Borst connector is described hereinafter, in connection with FIG. 4. As a result, the pressure transducer 66 is sealably enclosed within the body of fluid 64. In such arrangement, when needle 48 is inserted into reservoir 30, pressure variations in the CSF contained in reservoir 30 are transmitted through the fluid 64 and detected by transducer 66. Moreover, it will be readily apparent that CSF pressure in reservoir 30, and variations thereof, are transmitted to transducer 66 for read-out by monitor 62 immediately, i.e., in real time.

Figure 4:
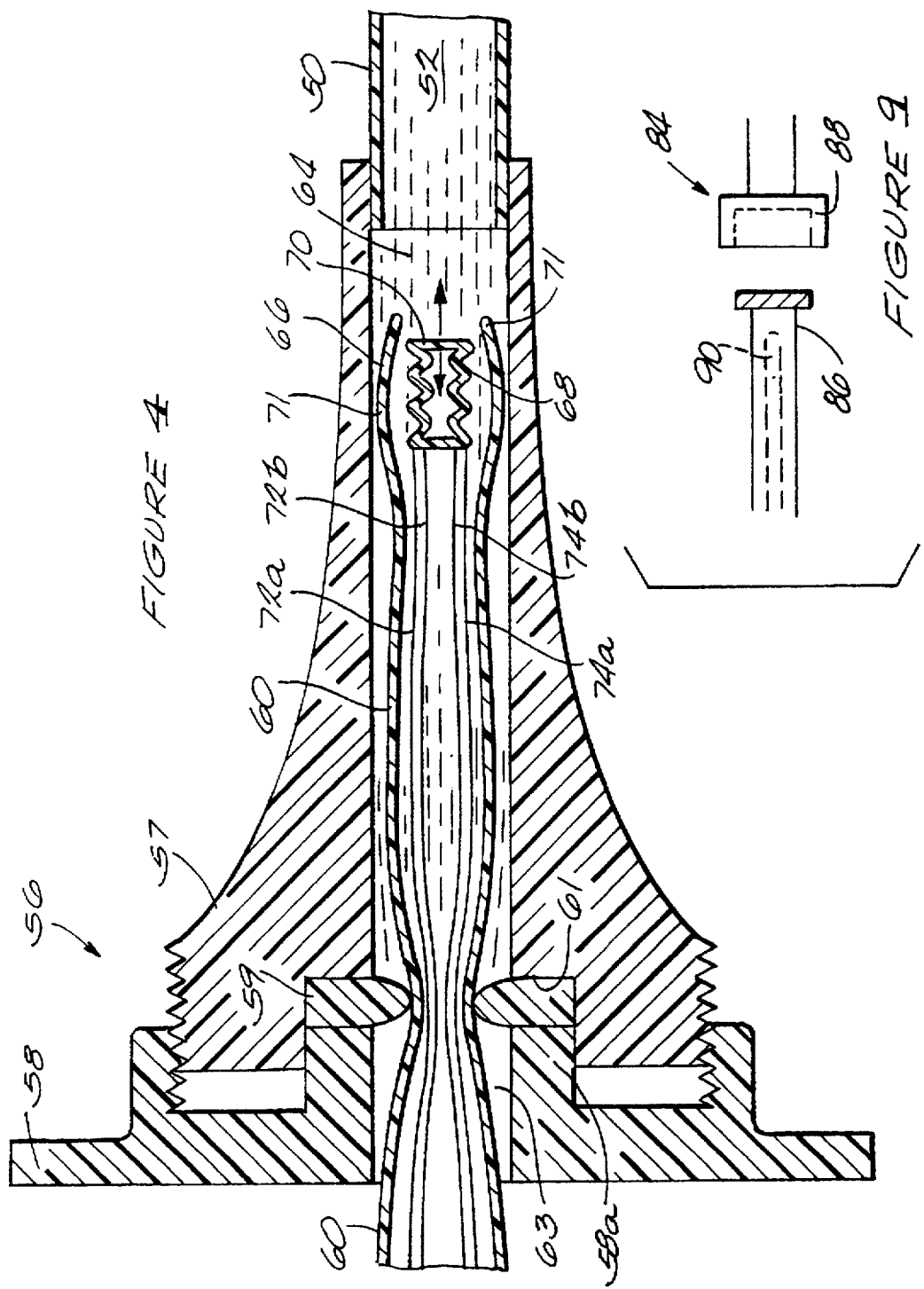
FIG. 4 is a sectional view taken along lines 4—4 of FIG. 3.

Referring to FIG. 4, there is shown Touhy-Borst catheter coupling device 56 additionally comprising an end member 57 having threads in engagement with the threads of nut 58. Catheter coupling device 56 is further provided with a washer 59, formed of compliant silicone or the like, positioned against a seat 61 of end member 57. Thus, when nut 58 is tightened, i.e., moved rightward as viewed in FIG. 4, an annular compression member 58a formed as part of nut 58 acts to compress the washer 59. Accordingly, the washer 59 is forced into bore 63 of the Touhy-Borst connector, which is in communication with passage 52. The washer pinches off catheter 60, and seals bore 63 to prevent fluid 64 from moving leftward past washer 59, as viewed in FIG. 4. Thus, nut 58, end member 57, and washer 59 collectively comprise a catheter sealing component. It will be seen that fluid 64 and pressure transducer 66 contained therein will be at the same pressure as CSF in reservoir 30, when needle 48 is inserted thereinto.

Referring further to FIG. 4, there is shown pressure transducer 66 comprising a deformable bellows 68 having a mirror, or highly light reflective surface 70, mounted thereto. Thus, as the pressure of fluid 64 changes, mirror 70 will move rightward or leftward, as viewed in FIG. 4, in accordance therewith. Bellows 66 and mirror 70 are joined to the end of catheter 60 by means of a stainless steel cap 71. FIG. 4 further shows incident and return optical fiber cables 72a and 72b, respectively, which are coupled between transducer 66 and ICP monitor 62 to provide a closed path for a light signal. The light signal is directed onto the mirror 70 from the incident fiber optic cable 72a, and received back by the cable 72b. It will be readily apparent that the path length of the light signal will change in corresponding relation to the movement of mirror 70, and therefore represent pressure variations in the adjacent fluid system. Accordingly, the light signal provides an accurate and precise measurement of CSF pressure in reservoir 30. At the same time, the fluid 64 prevents more than negligible amounts of CSF in reservoir 30 from flowing out through the aperture made through the reservoir wall 43 by needle 48. After pressure measurements have been made, the needle is withdrawn, and the silicone wall of reservoir 30 sealably forms over the aperture. Thus, no more than negligible amounts of CSF will be drawn out of shunt system 10 by the pressure measurement process. FIG. 4 further shows fiber optic cables 74a and 74b, which extend between transducer 66 and monitor 62 to provide a path for a reference light signal.

In a useful embodiment of the invention, ICP monitor 62 comprises a device manufactured by the Camino division of NeuroCare, and sold thereby under the name Ventrix. This device includes a numeric display 65 for reading out sensed pressure values.

As stated above, distal occluder 40 can be depressed to prevent outflow of CSF from valve 10 to the peritoneal catheter. When this is done, the pressure in reservoir 30 will be substantially the same as the pressure in the ventricle 16 connected to the reservoir 30 through a fluid path. Accordingly, shunt tap 46, together with an ICP monitor 62 as shown in FIG. 3, may be readily employed to monitor ICP, without need for the invasive procedure described above. Monitor 62 may also be employed to detect and record ICP variations over specified time intervals, such variations comprising pressure wave forms.

It will be readily apparent that by means of shunt tap device 46 and ICP monitor 62, patient ICP may be determined for a given patient over a period of time. Usefully, monitor 62 is designed so that its display 65 indicates negative pressure values for very low levels of ICP. Such capability enables a monitor user to readily distinguish between high and low pressure conditions in a patient, for example, to be able to determine which pressure condition is causing a headache, by merely observing whether displayed pressure is positive or negative, respectively.

Use of shunt tap 46 also allows "dynamic" pressure monitoring of a patient. That is, a number of pressure readings may be taken for different patient positions, such as lying in a supine position, sitting or standing positions, and lying in a prone position. The pressure information provided by dynamic monitoring can be very useful, for example, in detecting shunt system conditions such as blockage of the ventricular catheter.

Figure 5:
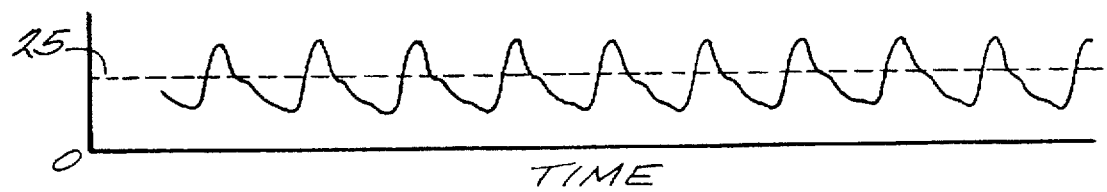
FIGS. 5–7 show respective pressure wave forms acquired by means of the embodiment shown in FIG. 3.

Referring to FIG. 5, there is shown a normal ICP wave form, as may be provided by the embodiment of the invention in FIG. 3. The average pressure is shown to be at 25 mm of water, approximately the middle of the range set forth above for a low pressure valve.

Figure 6:
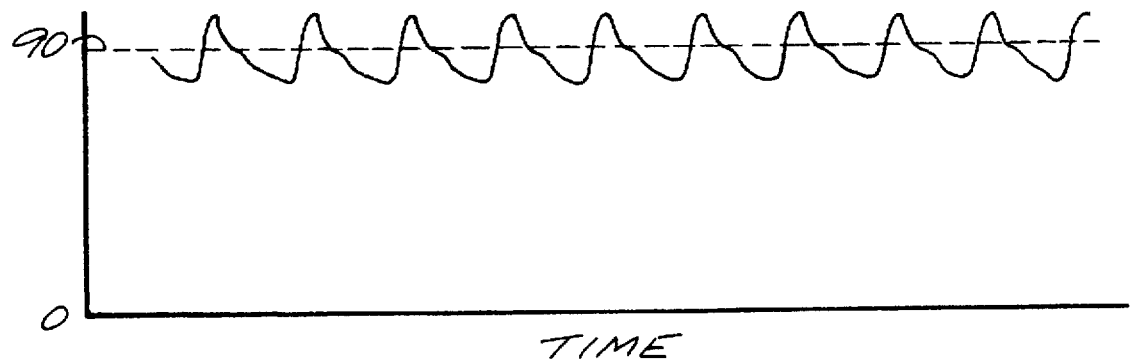

Referring to FIG. 6, there is shown an ICP wave form resulting from peritoneal catheter occlusion. In such event, ICP becomes greater than the opening/closing pressure of the valve. The average value of the wave forms is shown to be on the order of 90 mm of water in FIG. 6.

Figure 7:
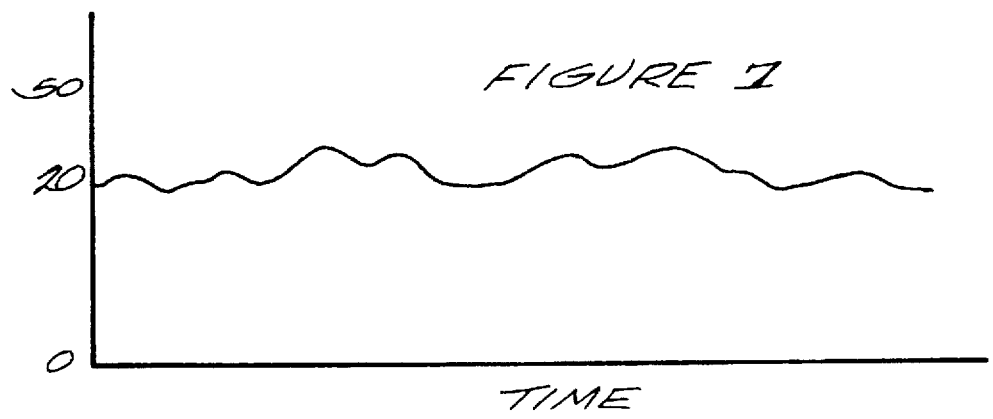

Referring to FIG. 7, there is shown the ICP wave form resulting from a partial ventricular catheter occlusion. It will be seen that the ICP wave form is altered, and pressure falls below the opening/closing pressure of the valve, such as to 20 mm of water as shown in FIG. 7. The waveform peaks are comparatively small due to the occurrence of damping in the shunt system.

Referring to FIG. 8, there is shown a modification 77 of the invention, wherein a Y-connector 78 is attached to the end of tubing 50 opposite needle 48. The Y-connector has one port which is joined to a Touhy-Borst coupler 56, as described above. The other port comprises a needle-less valve 80, which in turn comprises a piece of open conduit selectively closed by means of a cap 82. In addition to acquiring shunt pressure data, the embodiment shown in FIG. 8, by means of valve 80 after removal of cap 82, may be used to draw samples of CSF from reservoir 30, or to inject therapeutic drugs thereinto. Valve 80 may also be used to prime the shunt tap device with saline 64. Provision of valve 80 thus eliminates the need to use a syringe to inject saline solution into the shunt tap device. Needle-less valve 80 can also be used to readily connect the shunt tap to a luer-lock type connector.

Referring further to FIG. 8, there is shown the shunt tap device 77 inserted into a very simple shunt system 79, comprising only a reservoir 81 and a ventricular catheter 83. As stated above, a shunt system of such type may be used for chemotherapy. FIG. 8 serves to illustrate the minimal components of a shunt system with which the invention may be employed.

Referring to FIG. 9, there is shown a luer lock connector 84, comprising a female component 88 and a male component 86. In a further modification of the invention, connector 84 may be substituted for the Touhy-Borst connector of shunt tap 46, for use in engaging a pressure transducer 90 of a conventional type known as a strain gauge transducer.

Obviously, numerous other modifications and variations of the present invention are possible in light of the above teachings. It is therefore to be understood that within the scope of the disclosed concept, the invention may be practiced otherwise than as specifically described.

What is claimed is:

1. Shunt-tap apparatus for use in sensing CSF pressure data in a shunt implanted in a subject, wherein the shunt includes a reservoir lying along a CSF path of flow, said apparatus comprising:

means for temporarily forming an aperture to communicate with CSF contained in said reservoir;

coupling means for selectively engaging a pressure transducer comprising a component of a specified pressure-monitoring device; and pressure transmissive means positioned between said aperture forming means and said coupling means for transmitting CSF pressure data from said reservoir to said pressure transducer, while at the same time restricting CSF in said reservoir from passing through said aperture.

2. The apparatus of claim 1 wherein:

said aperture forming means comprises a hollow needle having a specified maximum gauge.

3. The apparatus of claim 2 wherein:

said pressure transmissive means comprises a fluid enclosure extending between said needle and said pressure transducer, and a selected fluid inserted to substantially fill said fluid enclosure.

4. The apparatus of claim 3 wherein:

said coupling means comprises means for retaining said pressure transducer in said fluid enclosure in contact with said inserted fluid, and for sealing said fluid enclosure to prevent more than negligible amounts of said fluid from flowing out of said fluid enclosure.

5. The apparatus of claim 4 wherein:

said coupling means comprises the catheter sealing component of a Touhy-Borst connector; and said fluid enclosure comprises, collectively, a portion of the bore of said Touhy-Borst connector and a passage through a length of flexible microbore tubing extending between said Touhy-Borst connector and said needle.

6. The apparatus of claim 5 wherein:

said pressure transducer comprises an optical device disposed to generate a light signal representing the pressure of a fluid adjacent to the optical device.

7. The apparatus of claim 4 wherein:

said coupling means comprises a luer lock connector.

8. The apparatus of claim 7 wherein:

said pressure transducer comprises a strain gauge device.

9. The apparatus of claim 4 wherein:

said fluid enclosure comprises, collectively, a Y-connector having two outlet ports and a single inlet port and a length of flexible microbore tubing extending between said needle and said inlet port, said coupling means being attached to said Y-connector to selectively seal one of said outlet ports, and a needle-less valve being attached to said Y-connector to selectively seal the other of said outlet ports.

10. The apparatus of claim 2 wherein:

the gauge of said needle does not exceed twenty-five gauge.

11. The apparatus of claim 1 wherein:

said pressure-monitoring device is provided with means for displaying negative pressure values to represent lower values of said CSF pressure data.

12. A method for sensing CSF pressure data in a shunt implanted in a subject, wherein said shunt has a reservoir lying along a CSF flow path, said method comprising the steps of:

temporarily forming an aperture through said reservoir, in communication with CSF contained therein;

transmitting CSF pressure data through said aperture from said reservoir to a pressure transducer at a selectively spaced-apart location, while at the same time preventing more than a negligible amount of CSF in the reservoir from passing through said aperture; and operating said pressure transducer to generate an information signal of selected type representing said transmitted CSF pressure data.

13. The method of claim 12 wherein:

said method includes the step of recording said specified information signal.

14. The method of claim 13 wherein:

said recording step comprises forming a set of graphic pressure waveforms from said information signal.

15. The method of claim 13 wherein:

said information signal represents CSF pressure data acquired when the subject is in each of a specified number of positions.

16. The method of claim 13 wherein:

said method includes the step of closing an outlet of a valve proximate to said reservoir to prevent flow of CSF away from said reservoir, so that the fluid pressure therein becomes substantially the same as the fluid pressure of a region within the subject to which the shunt is connected.

17. The method of claim 12 wherein:

said pressure data is transmitted from said reservoir to said pressure transducer in substantially real time.

18. A method for sensing CSF pressure data in a shunt implanted in a subject, wherein said shunt has a valve lying along a CSF flow path, said method comprising of the steps of:

temporarily forming an aperture to tap into said shunt, in communication with CSF contained therein, at a position along said path of flow which is proximal to said valve;

transmitting CSF pressure data through said aperture to a pressure transducer at a location selectively spaced-apart from said aperture, while at the same time preventing more than a negligible amount of CSF from passing through said aperture; and operating said pressure transducer to generate an information signal of selected type representing said transmitted CSF pressure data.

19. The method of claim 18 wherein:

said aperture forming step comprises inserting a hollow needle into a reservoir containing CSF, which lies along said path of flow proximal to said valve.

\* \* \* \* \*